United States Patent
Bernhardt et al.

(10) Patent No.: US 10,861,155 B2
(45) Date of Patent: Dec. 8, 2020

(54) LEARNING-BASED CORRECTION OF GRID ARTIFACTS IN X-RAY IMAGING

(71) Applicant: Siemens Healthcare GmbH, Erlangen (DE)

(72) Inventors: Philipp Bernhardt, Forchheim (DE); Boris Stowasser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/785,598

(22) Filed: Feb. 8, 2020

(65) Prior Publication Data
US 2020/0258222 A1 Aug. 13, 2020

(30) Foreign Application Priority Data
Feb. 8, 2019 (EP) .................................... 19156195

(51) Int. Cl.
| | |
|---|---|
| *A61B 6/00* | (2006.01) |
| *G06T 7/00* | (2017.01) |
| *G16H 30/40* | (2018.01) |
| *G06N 20/00* | (2019.01) |
| *G01N 23/04* | (2018.01) |

(52) U.S. Cl.
CPC .......... *G06T 7/0012* (2013.01); *A61B 6/4291* (2013.01); *A61B 6/4441* (2013.01); *A61B 6/4458* (2013.01); *G01N 23/04* (2013.01); *G06N 20/00* (2019.01); *G16H 30/40* (2018.01); *G06T 2207/10116* (2013.01); *G06T 2207/20081* (2013.01)

(58) Field of Classification Search
CPC ... A61B 6/4291; A61B 6/4441; A61B 6/4458; G01N 23/04
See application file for complete search history.

(56) References Cited

U.S. PATENT DOCUMENTS

| | | | |
|---|---|---|---|
| 7,050,618 B2 | 5/2006 | Belykh | |
| 2007/0104321 A1* | 5/2007 | Spahn | G21K 1/025 378/154 |

(Continued)

FOREIGN PATENT DOCUMENTS

| | | |
|---|---|---|
| DE | 102011080279 A1 | 2/2013 |
| EP | 1696366 A1 | 8/2006 |

(Continued)

OTHER PUBLICATIONS

European Search Report for European Patent Application No. 19156195.0-1124 dated Aug. 27, 2019, with English translation.

(Continued)

*Primary Examiner* — Dani Fox
(74) *Attorney, Agent, or Firm* — Lempia Summerfield Katz LLC

(57) ABSTRACT

A method for training a function of an X-ray system that has a positioning mechanism such as a C-arm, a detector, and, in a beam path in front of the detector, an anti-scatter grid. Positioning of the detector at a large number of different positions occurs. The positioning mechanism is deflected and/or distorted. Recording of at least one X-ray photograph in each of the positions then takes place, and the method further includes machine learning of artifacts generated by the anti-scatter grid from all X-ray photographs for the function.

15 Claims, 1 Drawing Sheet

(56) References Cited

U.S. PATENT DOCUMENTS

2011/0200169 A1    8/2011  Oikawa
2017/0319167 A1*  11/2017  Goto .................... A61B 6/5205
2018/0078221 A1*   3/2018  Petersilka ............ A61B 6/5282

FOREIGN PATENT DOCUMENTS

| JP | 2004242749 A | 9/2004 |
| JP | 2006231055 A | 9/2006 |
| JP | 2011167334 A | 9/2011 |
| JP | 2018068747 A | 5/2018 |

OTHER PUBLICATIONS

European Search Report for European Patent Application No. 19156195.0-1124 dated Aug. 27, 2019.
Japanese Office Action for Japanese Application No. 2019-227416 dated Aug. 4, 2020, with English translation.

* cited by examiner

LEARNING-BASED CORRECTION OF GRID ARTIFACTS IN X-RAY IMAGING

This application claims the benefit of European Patent Application No. EP19156195.0, filed Feb. 8, 2019, which is incorporated by reference in its entirety.

BACKGROUND

The present embodiments relate to operating an X-ray system.

During X-ray imaging, as a rule, scatter rays are produced at the object to be examined. While the actual effective radiation from the X-ray tube is oriented directly onto the detector or image carrier, the scatter radiation is not directed or has a direction that is different therefrom. The scatter radiation frequently causes a uniform dose distribution at the detector. As a rule, the scatter radiation decreases as the energy of the X-ray radiation increases. The scatter radiation fraction increases as the object thickness increases. The image quality and, for example, the signal-to-noise ratio are reduced by the scatter radiation.

A reduction in the scatter radiation is generally achieved by a focusing anti-scatter grid, which is arranged in front of the detector. The anti-scatter grid reduces the incidence of the scatter radiation, whereby the contrast of the X-ray image is increased. An anti-scatter grid of this kind is constructed from thin lead sheets. Located between the absorbing lead sheets are usually permeable spacers made of aluminum or cellulose. The sheets are parallel to the radiation, so the directed, desired radiation penetrates through the sheets while the scatter radiation is absorbed.

More recent developments use, for example, the technique of laser sintering to produce anti-scatter grids made, for example, of tungsten with a very good aspect ratio. In this connection, aspect ratio may be the ratio of gap width to gap height in the grid. This ratio is may, for example, be 1:10.

One problem, which occurs when using an anti-scatter grid, is the reproduction of the grid structure in the image. This provides that the reproduced grid structure overlays the actual image information. Without a correction of this grid structure, the use of this grid with the very good aspect ratios is not possible.

Until now, this problem has been solved by attempting to calibrate the X-ray system accordingly. This provides that corresponding recordings are obtained with the anti-scatter grid, but without examination object, and the reproductions of the grid in the case of photos with examination object are subtracted accordingly. In this way, the object data and, for example, the anatomical structures are retained on images, while the grid structures are reduced or even eliminated.

Despite calibrations of this kind, the grid structures are visible again in particular positions (e.g., of the C-arm). This is due to the fact that a C-arm is not infinitely rigid; instead, the C-arm is deflected and/or distorted due to the inherent weight as a function of the respective position in the three-dimensional space. This provides that in certain positions of the C-arm, the grid structure is not visible after this subtractive calibration, while in other positions, the grid structure is fully visible. Under some circumstances, the C-arm is distorted or deflected such that the orientation of X-ray source and X-ray detector changes in some positions of the C-arm by fractions of a degree. This is enough to not be able to sufficiently eliminate the corresponding grid structure in the image. Therefore, the signal-to-noise ratio increases, or grid artifacts may be identified as disruptive structures.

SUMMARY AND DESCRIPTION

The scope of the present invention is defined solely by the appended claims and is not affected to any degree by the statements within this summary.

The present embodiments may obviate one or more of the drawbacks or limitations in the related art. For example, pre-conditions are created in order to be able to eliminate artifacts of an anti-scatter grid in X-ray images more easily.

According to one aspect, a method is therefore provided for training a function of an X-ray system that has a positioning mechanism (e.g., a C-arm) having a detector and, in a beam path in front of the detector, an anti-scatter grid. The method includes positioning the detector at a large number of different positions. The positioning mechanism is deflected and/or distorted. The method also includes recording, in each case, at least one X-ray photograph in each of the positions and machine learning of artifacts generated by the anti-scatter grid from all X-ray photographs for the function in a first learning step A function of an X-ray system is therefore to be trained. Training may also be taken to be initial training of the X-ray system. The X-ray system may itself be capable of learning the characteristic behavior (e.g., with respect to a geometry).

The X-ray system may be a C-arm X-ray system or a system having robotic arms. The X-ray system may also include any other X-ray arrangement, however, in which the detector is provided with an anti-scatter grid, and both components may be swiveled or moved with respect to an object to be examined. With corresponding movements, as a rule, maladjustments, even if only minimal, of the detector always occur with respect to the ideal beam path. These maladjustments may have an effect on the visibility of the anti-scatter grid on the X-ray image obtained.

The positioning mechanism may be a C-arm or robotic arms. The X-ray tube is conventionally located at the one end of the C-arm, and the detector with anti-scatter grid is conventionally located at the other end of the C-arm. Since a C-arm of this kind with X-ray components may weigh several 100 kilos, in the case of movements of the C-arm in the three-dimensional space, deflections and distortions may occur due to the inherent weight alone. The extent of the deflection or distortion also definitively depends on the rigidity of the positioning mechanism or of the C-arm. For example, the extent of the deflection or distortion depends on the orientation of the positioning mechanism or of the C-arm in the space. If the C-arm is vertical, for example, then sometimes, the C-arm is deflected less than in cases in which the positioning mechanism or the C-arm is tilted.

A C-arm may be used as a positioning mechanism. In this case, the C-arm also includes the drive units, which bring the C-arm into the different positions and orientations. The positioning mechanism, however, may also be, for example, a robotic arm that positions and/or orients the detector correspondingly.

Basically, the X-ray system is capable of positioning the detector at different positions in the space. For example, a C-arm X-ray apparatus may position or site the detector on parts of a spherical surface. In each of these positions, the C-arm is tilted accordingly about one or more axes. In each of these positions, the C-arm or the positioning mechanism is deflected or distorted in accordance with a suspension, weight distribution, rigidity, etc.

At least one X-ray photograph is now taken in each of these positions. Depending on deflection and/or distortion, the grid structure of the anti-scatter grid may be identified to differing extents on the image. Ideally, with no deflection and distortion, the anti-scatter grid may be identified more as a filigree structure. With relatively high deflection or distortion, the structural elements of the grid structure will become wider since the grid aspects are no longer parallel to the beam path. Different reproductions of the anti-scatter grid therefore result in all positions of the detector. If, therefore, for example, the C-arm X-ray apparatus has two rotational degrees of freedom and the first rotational degree of freedom allows a rotation about 360 degrees, photos may be effected in a grid of, for example, five degrees, ten degrees, or the like. At the end of this 360 degrees, the C-arm is rotated further in the second degree of freedom about one grid element (e.g., likewise five degrees or ten degrees). The screening is then run through again in the first degree of freedom. In this way a, for example, spherical surface may be scanned.

The numerous X-ray photographs provide a data set that shows the effects of the geometric changes of the X-ray system in relation to the reproduction of the anti-scatter grid. From this data set, the artifacts of the anti-scatter grid in any position may now be learned for the specific function. The artifacts generated in each case correspond to reproduction components that are not produced or are produced not only by perpendicular projection of the anti-scatter grid onto the image plane. These may be, for example, widenings or blurrings of the grid structure.

Learning or training of the artifacts does not necessarily have to be in relation to the respective positions. Instead, it may be sufficient for the system to learn that a reproduced structure is precisely a grid structure of an anti-scatter grid. The system then identifies not just the anti-scatter grid in the ideal orientation parallel to the beam path, but also the anti-scatter grid, if the anti-scatter grid is tilted in one or more direction(s) relative to the beam path.

In an embodiment of the method, on each positioning of the detector, respective system geometry data of the X-ray system is supplied, which serves as input variables for machine learning. This system geometry data does not have to be available in every case. However, it is advantageous if the system geometry is available and may also be learned along with the respective image, so the respective classification for the function of the X-ray system may be performed more reliably.

It can be provided that each of the different positions of the detector is approached multiple times by the positioning mechanism for machine learning. Approaching one and the same position multiple times has the advantage that the varying behavior of the X-ray system may be taken into account. A first run to a grid point frequently gives rise to slightly different artifacts than a second run to the same grid point. This provides that when this grid point is approached multiple times and when the corresponding X-ray images are recorded multiple times accordingly, different artifacts, caused by the anti-scatter grid, are generated or reproduced. The artifacts may be averaged accordingly by a plurality of photos. The reliability with which the respective artifacts may be correctly identified may be increased as a result.

Specifically, it may be provided that each position or each grid point of a large number of grid points is approached from different directions. The deflection and/or distortion depends also on the history of the preceding movements of the positioning mechanism or of the C-arm. The system does not return completely to the initial state (e.g., undeflected state) with each movement. The deflections or distortions are not fully reversible therefore and instead, depend on the start position from which the detector has moved into the new position. Vibrations of the system or detector, including anti-scatter grid, also play a part here. Therefore, the vibrations typically depend on the respective drive. For example, a drive about one axis may cause different vibrations to a drive about a different axis. If the vibrations have not sufficiently subsided, then the vibrations have different effects on the artifacts, accordingly.

In a further development, the large number of different positions of the detector is arranged uniformly distributed over an entire system-based movement space of the X-ray system. Grid points are therefore uniformly distributed in that space that the detector may occupy. Idealized, the detector may be assumed as a point.

Machine learning, in addition to the first learning act, includes a second learning step that is identical to the first learning step. The anti-scatter grid is removed from the detector and removed from the beam path. In the first learning step, the artifacts of the anti-scatter grid actually present are therefore learned, while in the second learning step, the system learns what the images look like without the anti-scatter grid. In this way, the system may better identify the effects of the anti-scatter grid, so the effects may ultimately be eliminated better.

According to one development of the method, on recording the X-ray photographs, a phantom, which, optimally, does not generate any scatter radiation, is placed in the beam path. The phantom corresponds to an artificial object that is X-rayed by the X-ray radiation. The recorded X-ray images therefore contain not just a reproduction of the anti-scatter grid, but also a reproduction of the phantom. The reproduction components of the phantom and the reproduction components of the anti-scatter grid may be distinguished more reliably by machine learning. For example, the learning effect is therefore higher because the X-ray photographs are effected from different perspectives.

According to a further aspect, by way of simulation, virtual training data is obtained and is used, in addition to the X-ray photographs, for machine learning. This has the advantage that additional training data may be supplied quickly and inexpensively to improve the signal-to-noise ratio. Potentially, actual X-ray images have to be obtained for machine learning or training only, for example, regions of the movement space, and virtual training data may be used in other space portions owing to symmetries. Optionally, stronger vibrations may also be simulated, which may result with aging of the equipment and cause the possible enlargements of the artifacts. Optionally, virtual training data may also be obtained by overlaying X-ray images already obtained.

In one embodiment, it is also provided that an object X-ray photograph of an object is obtained, and artifacts of the anti-scatter grid are reduced or eliminated in this object X-ray photograph using the trained artifact. The output data of this automatic or machine-based learning or training is therefore used to partially or completely reduce the artifacts in the case of an actual X-ray photograph. As a result, a corrected object X-ray photograph is then produced substantially without the artifacts of the anti-scatter grid. In a simplified case, the grid structure of the anti-scatter grid is identified (e.g., position-specifically; in an object X-ray photograph) and subtracted from the object X-ray photograph by software. An X-ray photograph of the object that does not have any position-specific artifacts of the anti-scatter grid may therefore be obtained.

In one embodiment, in one application of the trained function, a method may also be supplied for operating an X-ray system that has a positioning mechanism (e.g., a C-arm) having a detector and, in a beam path in front of the detector, an anti-scatter grid. The method includes positioning the detector at a position. The positioning mechanism is deflected and/or distorted. An X-ray photograph is recorded in the position, and artifacts resulting with deflection and/or distortion of the positioning mechanism are corrected in the X-ray photograph by artifacts learned according to one of the above-described methods. The artifacts are caused by the anti-scatter grid.

According to a further aspect, a computer-implemented method is provided for generating object image data. The method includes receiving an object X-ray photograph, applying a function according to the above-mentioned method to the object-X-ray photograph for generating a corrected object-X-ray photograph, and supplying the corrected object-X-ray photograph as the object image data.

The method of one or more of the present embodiments may therefore be implemented in the framework of a computer-implemented method in which the object X-ray image is corrected of the artifacts according to the learned function.

According to a further aspect, an X-ray system is provided. The X-ray system includes a positioning mechanism and a recording device having a detector and an anti-scatter grid located in the beam path in front of the detector. The detector and the anti-scatter grid are attached to the positioning mechanism. With the positioning mechanism, the detector may be positioned at a large number of different positions in which the positioning mechanism is deflected and/or distorted as a function of position. With the recording device, in each case, at least one X-ray photograph may be generated in each of the positions, and the X-ray system is fitted with an arithmetic device for machine learning of artifacts generated by the anti-scatter grid from all X-ray photographs in a first learning step.

The X-ray system is, for example, a C-arm X-ray system or a different system in which the detector may be located at different positions. The positioning mechanism is used for this, to which the detector and the anti-scatter grid are secured. The positioning mechanism has already been explained in more detail above in connection with the method of one or more of the present embodiments. The recording device of the X-ray system also includes, in addition to the detector and the anti-scatter grid, an appropriate X-ray source. Machine learning is carried out with the arithmetic device, which may include, for example, one or more processors.

Automatic learning or machine learning may include supervised training, semi-supervised training, reinforced learning, and/or active learning. Machine learning may also include feature learning. Specifically, the parameters of the trained functions may be iteratively adapted in a plurality of training acts.

For example, the trained function may have a neural network, a support vector machine, a decision tree, and/or a Bayesian network. The trained function may be based on a k-means algorithm, a Q-learning algorithm, a genetic algorithm, and/or association rules. Specifically, a neural network may be a deep neural network, a convolutional neural network, or a convolutional, deep neural network. The neural network may be an adversarial network, a deep adversarial network, and/or a generative adversarial network.

The advantages and variation possibilities described above in connection with the method of one or more of the present embodiments apply analogously also to the X-ray system of one or more of the present embodiments, and vice versa.

Solutions of the present embodiments are described with reference to methods for operating an X-ray system, as well as corresponding X-ray systems, but also with reference to methods for training an X-ray system or corresponding X-ray systems. Features, advantages and alternative embodiments apply alternately to both the corresponding methods and the corresponding X-ray systems. In other words, the description for methods and systems for training may be developed with features that are described in connection with the methods and systems, and vice versa.

In general, the trained function (e.g., based on the learned artifacts) imitates cognitive functions. For example, the trained function is capable of adjusting to new circumstances and detecting and extrapolating corresponding patterns.

DETAILED DESCRIPTION

Figure 1:
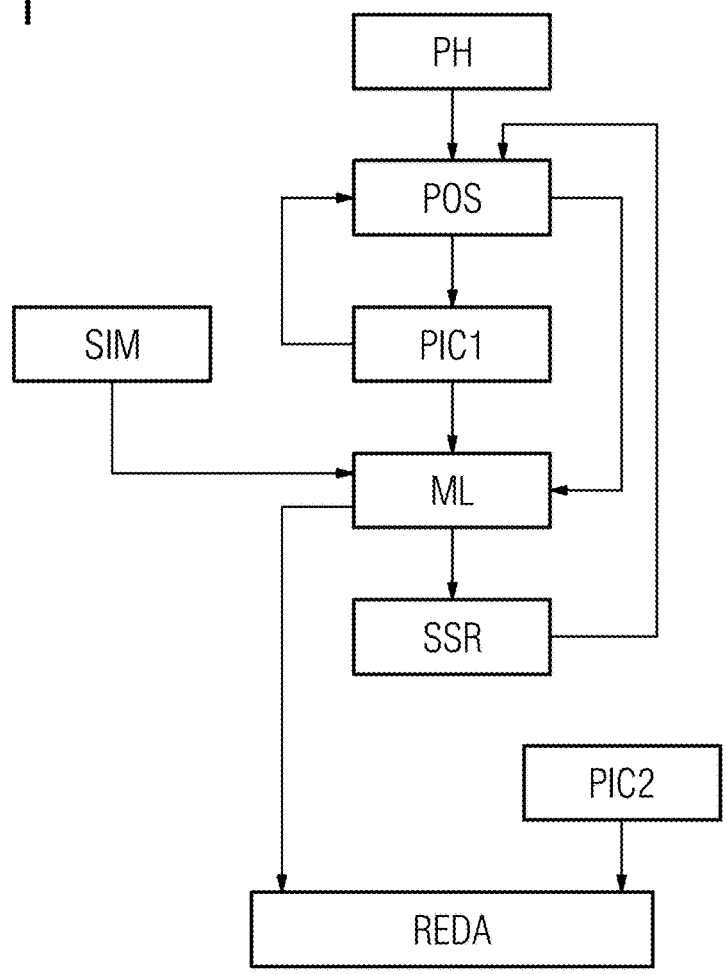
FIG. 1 shows an exemplary schematic method sequence.

The example of FIG. 1 shows a schematic sequence diagram of one embodiment of a method for operating an X-ray system. In an optional act PH, a phantom is placed in a beam path of the X-ray system and, for example, of the C-arm X-ray system. The phantom may be an object that has similar forms and structures to a natural anatomic structure. The phantom may not cause any, or only very little, scatter radiation in the beam path when the phantom is X-rayed by X-ray radiation.

In a positioning act POS, a detector of the X-ray system is positioned at a particular position in the space. Located in front of the detector in the beam path is an anti-scatter grid. Corresponding to the beam path and located opposite the detector is an X-ray source. In a C-arm system, as is known, the X-ray source is moved with the detector since both components are fastened to the C-arm arms.

In a recording act PIC1, an X-ray photograph is taken. The detector is then re-positioned, so the method returns to the positioning act POS. Consequently, the detector is re-oriented and positioned in the space. An X-ray photograph is then taken in this new position of the detector again. These acts POS and PIC1 are repeated until all grid points in a specified movement space of the detector have been assumed one or more times. In one embodiment, the entire movement space of the detector or recording system is uniformly provided with grid points. For example, the grid points may be located on a uniform grid that reaches over the entire movement space. The grid points may be defined, for example, in that the recording system in each case moves by constant angles discretely about a first axis and, similarly, discretely about a second perpendicular axis. Therefore, for example, the system may be moved from one grid point to the next by five or ten degrees (or another degree value).

In each position or orientation of the detector, including the anti-scatter grid, the system or the positioning mechanism of the X-ray system is characteristically distorted or deflected. Even if such deflections or distortions are small and scarcely perceptible, the deflections or distortions sometimes play a crucial role in the reproduction of the anti-scatter grid on the detector. Since the extent of the deflections and distortions depends on the respective positioning of the detector or of the entire imaging system, the artifacts that result on imaging correspondingly also depend on the detector positioning.

Depending on the system, positioning of a detector may occur in different ways. With C-arm X-ray systems, fixed movement paths on one or more spherical surfaces are specified in a rough approximation. With robot-based X-ray systems, a detector is linearly displaced, for example, about a first axis, and swiveled about one or more axes. In this case, for example, the detector position may be adjusted completely independently of the position of the X-ray source. Robot-based X-ray systems may be mounted on the floor or on the ceiling. Independently thereof, intrinsic deflections or distortions of the system (e.g., of the robotic arm) occur at all positionings and orientations of the detector.

These system-related deflections and distortions often may not be reproduced, or only with much difficulty. In a first position, the system is distorted in a first way. If the system is brought into a second position, the system is deflected or distorted in a second way, which depends on the first way. This is due to the fact that on a change in position, the system does not always return to the same starting position. Starting from a third position, a different deflection or distortion results in the second position, which is different with a start from the first position.

In an automatic learning step or machine learning step ML, the artifacts caused by the anti-scatter grid are now learned from the large number of recorded X-ray photographs for a function of the X-ray system. Sometimes, it may be advantageous to also take into account the position data optionally supplied from the positioning act POS. The system therefore learns the artifacts caused by the anti-scatter grid in many or all possible positions. The movement history and, for example, the position of the detector before the in each case current detector position are optionally also learned during learning. Therefore, for example, a current X-ray photograph, a current position, and a preceding position are linked in one learning step.

Additional virtual training images may be generated to increase the volume of training data for training of the system. Virtual training images of this kind may be obtained by a simulation in a simulations act SIM. Therefore, these virtual training images may be obtained by a virtual anti-scatter grid using a corresponding simulation. The basis of the training data may be increased hereby, and the quality of learning may therefore be improved.

In a further method act of scattered rays grid removal SSR, the anti-scatter grid may be removed from the beam path between the X-ray source and the X-ray detector. X-ray photographs that do not have any artifacts that result due to the anti-scatter grid may be obtained hereby. Optionally, only fluoroscopy images of the phantom now remain on the X-ray photographs. Based on these images, the learning system may learn the difference between the structures of the phantom and the structures of the anti-scatter grid. Following removal of the anti-scatter grid, the method is therefore continued with the positioning act POS, and the same X-ray photographs are obtained as before with the anti-scatter grid.

Machine learning ML occurs, therefore, with images that show the scattered rays grid, including artifacts, with images, which were recorded without anti-scatter grid and optionally also with virtual training images from the simulation SIM. The thus trained system or the thus trained function may now be applied in practical operation. For this, object X-ray photographs of an object to be examined (e.g., part of a human body) are obtained in a further recording act PIC2. The photo or the photos resulted with the anti-scatter grid. In an image processing act REBA, the grid structures of the anti-scatter grid, including the position-dependent artifacts, which also emanate from the anti-scatter grid, are reduced or eliminated from the object X-ray photographs by the learned function. The current position data of the detector position or the position of the recording device is optionally also used for this. This position data may again also include calculating information about the orientation of the detector or the recording device.

Figure 2:
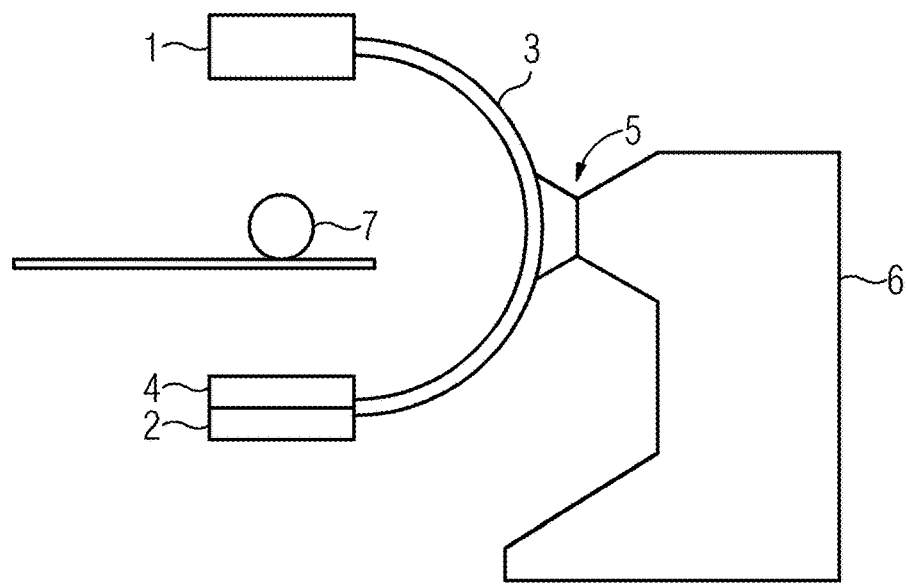
FIG. 2 shows a sketch of one embodiment of an X-ray system.

FIG. 2 schematically shows an exemplary embodiment of an X-ray system. In the present case, this is a C-arm X-ray system. The C-arm X-ray system has an X-ray source 1 and a detector 2 on the opposing arms of a C-arm 3. An anti-scatter grid 4 is located directly on the detector 2 in the beam path between the X-ray source 1 and the detector 2. The X-ray source 1 together with the detector 2 and optionally the anti-scatter grid 4 used form a recording device. The C-arm 3, optionally together with a pivot joint or swivel joint 5 and corresponding drives for the C-arm 3, form a positioning mechanism for the recording device 1, 2, 4. An appropriate controller and image processing device or an appropriate arithmetic device may be accommodated in a device body 6.

The X-ray source 1 and the detector 2 with the removable anti-scatter grid 4 may alternatively also be held and positioned by other holding mechanisms, such as robotic arms. Positioning may also include orientation.

Located in the beam path between the X-ray source 1 and the detector 2 is optionally a phantom 7 or the object that is actually to be examined. As a rule, the object generates scatter radiation that is largely eliminated by the anti-scatter grid 4 with ideal orientation of the X-ray source 1 and the detector 2 since the anti-scatter grid 4 may be orientated in relation to the beam path. A sharp image of the anti-scatter grid 4 then results on the detector 2, and this may be easily eliminated by simple subtraction. If, however, the C-arm 3 is tilted or rotated, this may lead to the one arm of the C-arm 3 being deflected or distorted slightly differently than the other arm of the C-arm 3. In this case, additional artifacts are produced on the grid structure in the X-ray image. These may be eliminated with the aid of the trained system, which "knows" the artifacts in all possible positions of the detector 2 or the recording device. The trained system may also remove the actual grid structure from the X-ray photographs.

In a specific example, a learning-based method is applied based on "calibration runs" during production or by the user in order to learn the grid structures and optionally eliminate the grid structures, including the artifacts.

The system is trained, for example, in two learning acts A and B. Learning act A is configured as follows: a) The anti-scatter grid is used; b) an entire space of the possible movement trajectories is adequately precisely scanned (e.g., increment of five or ten degrees); c) radiation is activated, and the resulting image is stored for each scan point; d) in addition, the system geometry for this point may also be stored; and e) optionally, an anatomical phantom may also be positioned in the beam path.

Learning act B is configured as follows: f) The grid is removed; g) an entire space of the possible movement trajectories is adequately precisely scanned (e.g., increment of five or ten degrees); h) radiation is activated, and the resulting image is stored for each scan point; i) in addition, the system geometry for this point may also be stored; and
j) optionally, an anatomical phantom may also be positioned in the beam path.

The data from learning acts A and B is used for the learning-based method in order to train the learning-based method. Training optionally takes place by way of supervised training, semi-supervised training, unsupervised training, or the like. A neural network, a support vector machine, or the like may be used for this. The trained network or the trained function is then used in the application to eliminate the grid structure, including artifacts.

Due to the application of a learning-based method, precise knowledge of the reproduction is not necessary for correction. Any change does not have to be analytically re-determined; instead, the change may be solved by a new calibration run.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for training a function of an X-ray system, the X-ray system including a positioning mechanism, a detector, and, in a beam path in front of the detector, an anti-scatter grid, the method comprising:
    positioning the detector at a number of different positions, wherein the positioning mechanism is deflected, distorted, or deflected and distorted;
    recording in each case at least one X-ray photograph in each of the number of different positions; and
    machine learning artifacts generated by the anti-scatter grid from all of the X-ray photographs for the function in a first learning step.

2. The method of claim 1, wherein on each positioning of the detector, respective system geometry data of the X-ray system is supplied, the system geometry data serving as input variables for machine learning.

3. The method of claim 1, wherein each of the number of different positions of the detector for machine learning is approached multiple times by the positioning mechanism.

4. The method of claim 3, wherein each of the number of different positions is approached from different directions.

5. The method of claim 1, wherein the number of different positions of the detector is arranged uniformly distributed over an entire system-based movement space of the X-ray system.

6. The method of claim 1, wherein the machine learning, in addition to the first learning step, comprises a second learning step, the second learning step being identical to the first learning step, and
    wherein the anti-scatter grid is removed from the detector and removed from the beam path in the second learning step.

7. The method of claim 1, wherein on recording the X-ray photographs, a phantom that does not generate any scatter radiation is placed in the beam path.

8. The method of claim 1, further comprising obtaining virtual training data by way of simulation,
    wherein, in addition to the X-ray photographs, the obtained virtual training data is used for machine learning.

9. The method of claim 1, wherein an object X-ray photograph is obtained from an object, and artifacts of the anti-scatter grid are reduced or eliminated in the object X-ray photograph by the trained function.

10. The method of claim 1, wherein the positioning mechanism includes a C-arm.

11. A method for operating an X-ray system, the X-ray system including a positioning mechanism, a detector, and in a beam path in front of the detector, an anti-scatter grid, the method comprising:
    positioning the detector at a position, wherein the positioning mechanism is deflected, distorted, or deflected and distorted;
    recording an X-ray photograph in the position; and
    correcting artifacts resulting, which are caused by the anti-scatter grid, in the X-ray photograph with deflection, distortion, or deflection and distortion of the positioning mechanism by artifacts learned according to a method for training a function of the X-ray system, the method for training the function of the X-ray system comprising:
        positioning the detector at a number of different positions, wherein the positioning mechanism is deflected, distorted, or deflected and distorted;
        recording in each case at least one X-ray photograph in each of the number of different positions; and
        machine learning artifacts generated by the anti-scatter grid from all of the X-ray photographs for the function in a first learning step.

12. The method of claim 11, wherein the positioning mechanism comprises a C-arm.

13. A computer-implemented method for generating object image data, the computer-implemented method comprising:
    receiving an object X-ray photograph;
    generating a corrected object-X-ray photograph, the generating comprising applying a trained function to the object-X-ray photograph, such that artifacts of the anti-scatter grid are reduced or eliminated in the object X-ray photograph; and
    supplying the corrected object X-ray photograph as the object image data.

14. An X-ray system comprising:
    a positioning mechanism;
    a recording device including a detector and an anti-scatter grid located in a beam path in front of the detector, wherein the detector and the anti-scatter grid are attached to the positioning mechanism, wherein with the positioning mechanism, the detector is positionable at a large number of different positions in which the positioning mechanism is deflected, distorted, or deflected and distorted as a function of position, and wherein with the recording device, in each case at least one X-ray photograph is generatable in each of the number of different positions; and
    a processor configured for machine learning of artifacts generated by the anti-scatter grid from all the X-ray photographs in a first learning step.

15. The X-ray system of claim 14, wherein the X-ray system is configured as a C-arm X-ray system or a robotic arm-based X-ray system.

* * * * *